US009335256B2

(12) United States Patent
Takemura

(10) Patent No.: US 9,335,256 B2
(45) Date of Patent: May 10, 2016

(54) TECHNIQUE FOR MEASURING COLOR OF MEASUREMENT IMAGE

(71) Applicant: CANON KABUSHIKI KAISHA, Tokyo (JP)

(72) Inventor: Taichi Takemura, Abiko (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/170,411

(22) Filed: Jan. 31, 2014

(65) Prior Publication Data

US 2014/0226192 A1 Aug. 14, 2014

(30) Foreign Application Priority Data

Feb. 14, 2013 (JP) ................................ 2013-027143

(51) Int. Cl.
*H04N 1/46* (2006.01)
*G01N 21/27* (2006.01)
*G03G 15/00* (2006.01)

(52) U.S. Cl.
CPC ............ *G01N 21/27* (2013.01); *G03G 15/5062* (2013.01); *G03G 2215/0164* (2013.01); *G03G 2215/2006* (2013.01)

(58) Field of Classification Search
None
See application file for complete search history.

(56) References Cited

U.S. PATENT DOCUMENTS

| 5,132,786 | A | * | 7/1992 | Ishiwata | 358/500 |
| 5,204,755 | A | * | 4/1993 | Taga et al. | 358/400 |
| 5,650,863 | A | * | 7/1997 | Utagawa | G03G 21/046 358/475 |
| 5,750,985 | A | * | 5/1998 | Suzuki | H04N 1/486 250/226 |
| 5,751,451 | A | * | 5/1998 | Ogoshi et al. | 358/527 |
| 5,848,188 | A | * | 12/1998 | Shibata | G01B 11/2518 348/132 |

(Continued)

FOREIGN PATENT DOCUMENTS

JP 06-152872 (A) 5/1994
JP 2001-211335 8/2001

(Continued)

OTHER PUBLICATIONS

U.S. Appl. No. 14/171,666, filed by Taichi Takemura on Feb. 3, 2014.

(Continued)

*Primary Examiner* — Madelein Nguyen
(74) *Attorney, Agent, or Firm* — Fitzpatrick, Cella, Harper & Scinto

(57) ABSTRACT

A test chart on which measurement images are formed is conveyed in one direction. When the measurement images pass a color sensor, they undergo pre-scanning. A color sensor accumulation time is determined for each measurement image according to the pre-scanning. The test chart is subsequently conveyed in the one direction, whereupon the conveyance direction is changed. In this way, after the color sensor has completed pre-scanning for all of the measurement images, the test chart is once again conveyed toward the color sensor. When the test chart passes the color sensor again, main scanning of the measurement images is executed.

19 Claims, 10 Drawing Sheets

(56) References Cited

U.S. PATENT DOCUMENTS

| | | | | |
|---|---|---|---|---|
| 5,912,724 | A * | 6/1999 | Sakaguchi | 355/35 |
| 6,160,972 | A * | 12/2000 | Shimazu | G03G 15/5058 399/299 |
| 6,577,341 | B1 * | 6/2003 | Yamada | H04N 9/045 348/218.1 |
| 6,833,926 | B1 * | 12/2004 | Takano et al. | 358/1.15 |
| 7,014,289 | B1 * | 3/2006 | Matsuda | B41J 29/393 347/19 |
| 7,773,895 | B2 | 8/2010 | Zaima | |
| 2002/0085081 | A1 * | 7/2002 | Tanimoto | H04N 1/233 347/115 |
| 2005/0046653 | A1 * | 3/2005 | Yamazaki | B41J 2/2139 347/15 |
| 2007/0230978 | A1 * | 10/2007 | Zaima | 399/49 |
| 2008/0225102 | A1 * | 9/2008 | Tomita | B41J 2/473 347/129 |
| 2008/0259109 | A1 * | 10/2008 | Uchida | B41J 11/425 347/14 |
| 2009/0040584 | A1 * | 2/2009 | Han | B41J 2/471 359/212.1 |
| 2009/0296172 | A1 * | 12/2009 | Iwatsuka | 358/509 |
| 2010/0149489 | A1 * | 6/2010 | Kikawa | A61B 3/102 351/206 |
| 2011/0076040 | A1 * | 3/2011 | Uchidate et al. | 399/49 |
| 2011/0150510 | A1 * | 6/2011 | Kondo | G03G 15/043 399/51 |
| 2012/0033276 | A1 * | 2/2012 | Zaima | 358/518 |
| 2012/0092687 | A1 * | 4/2012 | Hirai | 358/1.9 |
| 2012/0099165 | A1 * | 4/2012 | Omori | G03G 15/5058 358/475 |
| 2012/0201554 | A1 * | 8/2012 | Ishihara et al. | 399/51 |
| 2012/0229546 | A1 * | 9/2012 | Okada et al. | 347/14 |
| 2013/0094039 | A1 * | 4/2013 | Takemura | 358/1.9 |
| 2013/0107290 | A1 * | 5/2013 | Lin et al. | 358/1.9 |
| 2013/0136474 | A1 * | 5/2013 | Itagaki | 399/49 |
| 2013/0156445 | A1 * | 6/2013 | Takemura | 399/15 |
| 2013/0243451 | A1 * | 9/2013 | Hirota et al. | 399/39 |
| 2014/0125982 | A1 * | 5/2014 | Takemura | 356/421 |
| 2014/0226192 | A1 * | 8/2014 | Takemura | G03G 15/5062 358/504 |
| 2014/0233049 | A1 * | 8/2014 | Takemura | H04N 1/0005 358/1.12 |
| 2015/0276622 | A1 * | 10/2015 | Otani | G01N 21/9501 356/237.5 |

FOREIGN PATENT DOCUMENTS

| | | |
|---|---|---|
| JP | 2006-304200 | 11/2006 |
| JP | 2007274438 A | 10/2007 |
| JP | 2009004865 A | 1/2009 |

OTHER PUBLICATIONS

Chinese Official Action dated Jan. 4, 2016, in counterpart Chinese Patent Application No. 201410050593.2, and English translation thereof.

* cited by examiner

FIG. 4

| NUMBER | C | M | Y | K |
|---|---|---|---|---|
| 1 | 0 | 0 | 0 | 0 |
| 2 | 50 | 0 | 0 | 0 |
| 3 | 100 | 0 | 0 | 0 |
| 4 | 0 | 50 | 0 | 0 |
| 5 | 50 | 50 | 0 | 0 |
| 6 | 100 | 50 | 0 | 0 |
| 7 | 0 | 100 | 0 | 0 |
| 8 | 50 | 100 | 0 | 0 |
| 9 | 100 | 100 | 0 | 0 |
| 10 | 0 | 0 | 50 | 0 |
| 11 | 50 | 0 | 50 | 0 |
| 12 | 100 | 0 | 50 | 0 |
| 13 | 0 | 0 | 100 | 0 |
| 14 | 50 | 0 | 100 | 0 |
| 15 | 100 | 0 | 100 | 0 |
| 16 | 0 | 50 | 50 | 0 |
| 17 | 50 | 50 | 50 | 0 |
| 18 | 100 | 50 | 50 | 0 |
| 19 | 0 | 50 | 100 | 0 |
| 20 | 50 | 50 | 100 | 0 |
| 21 | 100 | 50 | 100 | 0 |
| 22 | 0 | 100 | 50 | 0 |
| 23 | 50 | 100 | 50 | 0 |
| 24 | 100 | 100 | 50 | 0 |
| 25 | 0 | 100 | 100 | 0 |
| 26 | 50 | 100 | 100 | 0 |
| 27 | 100 | 100 | 100 | 0 |
| 28 | 0 | 0 | 0 | 50 |
| 29 | 50 | 0 | 0 | 50 |
| 30 | 100 | 0 | 0 | 50 |
| 31 | 0 | 50 | 0 | 50 |
| 32 | 50 | 50 | 0 | 50 |
| 33 | 100 | 50 | 0 | 50 |
| 34 | 0 | 100 | 0 | 50 |
| 35 | 50 | 100 | 0 | 50 |
| 36 | 100 | 100 | 0 | 50 |
| 37 | 0 | 0 | 50 | 50 |
| 38 | 50 | 0 | 50 | 50 |
| 39 | 100 | 0 | 50 | 50 |
| 40 | 0 | 0 | 100 | 50 |
| 41 | 50 | 0 | 100 | 50 |
| 42 | 100 | 0 | 100 | 50 |
| 43 | 0 | 50 | 50 | 50 |
| 44 | 50 | 50 | 50 | 50 |
| 45 | 100 | 50 | 50 | 50 |
| 46 | 0 | 50 | 100 | 50 |
| 47 | 50 | 50 | 100 | 50 |
| 48 | 100 | 50 | 100 | 50 |
| 49 | 0 | 100 | 50 | 50 |
| 50 | 50 | 100 | 50 | 50 |
| 51 | 100 | 100 | 50 | 50 |
| 52 | 0 | 100 | 100 | 50 |
| 53 | 50 | 100 | 100 | 50 |
| 54 | 100 | 100 | 100 | 50 |
| 55 | 0 | 0 | 0 | 100 |
| 56 | 50 | 0 | 0 | 100 |
| 57 | 100 | 0 | 0 | 100 |
| 58 | 0 | 50 | 0 | 100 |
| 59 | 50 | 50 | 0 | 100 |
| 60 | 100 | 50 | 0 | 100 |
| 61 | 0 | 100 | 0 | 100 |
| 62 | 50 | 100 | 0 | 100 |
| 63 | 100 | 100 | 0 | 100 |
| 64 | 0 | 0 | 50 | 100 |
| 65 | 50 | 0 | 50 | 100 |
| 66 | 100 | 0 | 50 | 100 |
| 67 | 0 | 0 | 100 | 100 |
| 68 | 50 | 0 | 100 | 100 |
| 69 | 100 | 0 | 100 | 100 |
| 70 | 0 | 50 | 50 | 100 |
| 71 | 50 | 50 | 50 | 100 |
| 72 | 100 | 50 | 50 | 100 |
| 73 | 0 | 50 | 100 | 100 |
| 74 | 50 | 50 | 100 | 100 |
| 75 | 100 | 50 | 100 | 100 |
| 76 | 0 | 100 | 50 | 100 |
| 77 | 50 | 100 | 50 | 100 |
| 78 | 100 | 100 | 50 | 100 |
| 79 | 0 | 100 | 100 | 100 |
| 80 | 50 | 100 | 100 | 100 |
| 81 | 100 | 100 | 100 | 100 |

TECHNIQUE FOR MEASURING COLOR OF MEASUREMENT IMAGE

BACKGROUND OF THE INVENTION

1. Field of the Invention

The present invention relates to a technique for measuring color in a measurement image for maintaining color stability in an image forming apparatus.

2. Description of the Related Art

In order to maintain color stability in an image forming apparatus, it is necessary to scan a measurement image (test pattern) and adjust various image processing conditions, image forming conditions, and the like. The test pattern is scanned by a color separation type color sensor, and the appropriate exposure time differs for each color. Japanese Patent Laid-Open No. 2007-274438 (Patent Document 1) proposes a technique in which the accumulation time of light receiving elements in a color sensor is changed according to the color and density of the formed image pattern. Accordingly, it is possible to detect the color and density of the image pattern with sufficient accuracy for any color and density of an image pattern.

However, since the appropriate accumulation time is determined by scanning a region that comprises the front half of one image pattern and the remaining region comprising the latter half of the image pattern is measured using the determined accumulation time, the size of the image pattern must be increased sufficiently. If the size per image pattern increases, the number of sheets needed will also increase. For example, this is because there are tens to hundreds of image patterns for creating a color matching profile such as an ICC profile. ICC is an abbreviation for International Color Consortium.

SUMMARY OF THE INVENTION

The present invention establishes a color measurement technique by which it is possible to reduce the number of sheets while suppressing an increase in the size of the measurement images.

The present invention provides an image forming apparatus comprising: an image forming unit configured to form a measurement image on a sheet; a conveyance unit configured to convey the sheet; a measurement unit configured to measure the measurement image by accumulating reflected light from the measurement image on the sheet conveyed by the conveyance unit; a control unit configured, after the measurement unit measures the measurement image on the sheet in a first scan, to cause the conveyance unit to convey the sheet once again toward the measurement unit, and cause the measurement unit to measure the measurement image on the sheet in a second scan; and a determination unit configured, based on a measurement result of the measurement unit in the first scan, to determine a reflected light accumulation time during which the measurement unit accumulates reflected light from the measurement image in the second scan.

The present invention provides a method of controlling an image forming apparatus including a measuring unit, the method comprising: forming a measurement image on a sheet; conveying the sheet on which the measurement image is formed; measuring, with the measuring unit the measurement image by accumulating reflected light from the measurement; after the measurement unit measures the measurement image on the sheet in a first scan, conveying the sheet once again toward the measurement unit, and measuring the measurement image on the sheet in a second scan; and determining, based on a measurement result of the measurement unit in the first scan, a reflected light accumulation time during which the measurement unit accumulates reflected light from the measurement image in the second scan.

Further features of the present invention will become apparent from the following description of embodiments with reference to the attached drawings. Each of the embodiments of the present invention described below can be implemented solely or as a combination of a plurality of the embodiments or features thereof where necessary or where the combination of elements or features from individual embodiments in a single embodiment is beneficial.

BRIEF DESCRIPTION OF THE DRAWINGS

FIG. 4 is a table showing an example of image signal values for generating a test pattern.

DESCRIPTION OF THE EMBODIMENTS

Image Forming Apparatus

In the present embodiment, pre-scanning is executed first as a first scan on all measurement images while a sheet is conveyed. In the present embodiment, after pre-scanning for all measurement images is complete, the sheet is conveyed once again toward a measuring unit and main scanning is executed as a second scan. By conveying the sheet on which the measurement images have been recorded to the measuring unit two times or more in this way, a color measurement technique can be established by which it is possible to reduce the number of sheets while suppressing an increase in the size of the measurement images.

An image forming apparatus 100 according to an embodiment will be described with reference to FIG. 1. Note that in the present embodiment, an electrophotographic type of printer is used as an example of an image forming apparatus. However, the present invention can be applied to an inkjet printer that includes an image forming unit that forms an image on a sheet by discharging ink, or to a sublimation type of printer that includes an image forming unit that forms an image on a sheet by causing the ink in an ink ribbon to sublimate with a head.

Image Forming Apparatus

In the present embodiment, a method for resolving the above-mentioned problem will be described using an electrophotographic type of laser beam printer. In the present embodiment, an electrophotographic type of method will be employed as an example of the image forming method. However, the present invention can be applied to an inkjet type or a sublimation type of method. Note that an image forming unit for forming an image on a sheet by discharging ink and a fixing unit (drying unit) for drying ink are used in an inkjet type of method.

Figure 1:
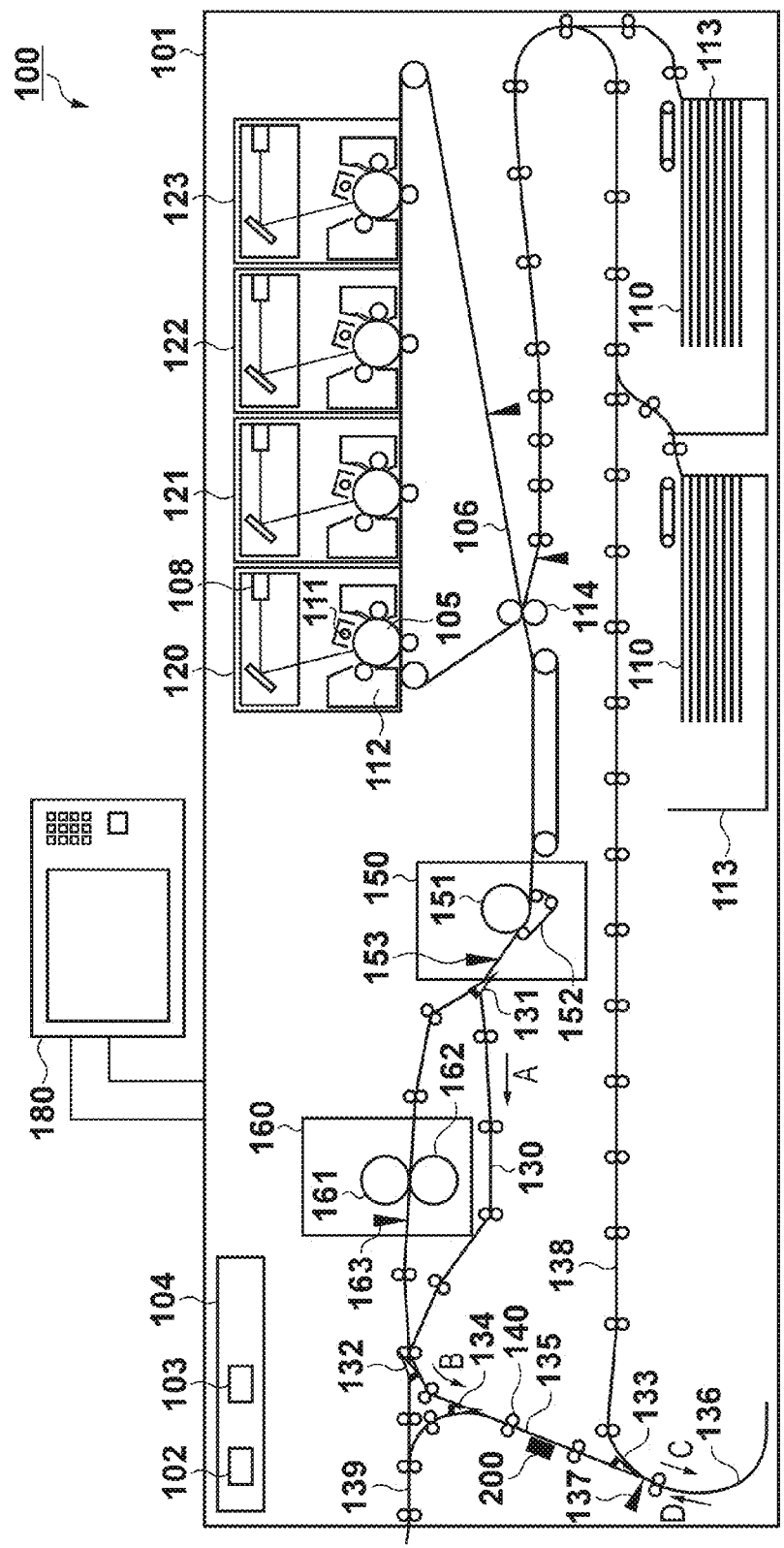
FIG. 1 is a schematic configuration diagram of an image forming apparatus.

FIG. 1 is a cross-sectional diagram showing a structure of the image forming apparatus 100. The image forming apparatus 100 includes a housing 101. Mechanisms for configuring a printer unit 1201, and a control board storing unit 104 are provided in the housing 101. The control board storing unit 104 stores an engine control unit 102 that performs control related to printing procedure processes (e.g., paper feeding processing) performed by the mechanisms, and a printer controller 103 that performs image processing and the like.

As shown in FIG. 1, four stations 120, 121, 122, and 123 that correspond to Y, M, C, and K are provided in the printer unit. The stations 120, 121, 122, and 123 are image forming units that transfer toner to a sheet to form an image. Here, YMCK is an abbreviation for yellow, magenta, cyan, and black. The stations are configured by substantially the same parts. A photosensitive drum 105 is a type of image carrying member that is charged to a uniform surface potential by a primary charger 111. A latent image is formed on the photosensitive drum 105 by laser light output from a laser 108. A developer 112 forms a toner image by developing the latent image using color materials (toner). The toner image (visible image) undergoes primary transfer onto an intermediate transfer member 106. The visible image that is formed on the intermediate transfer member 106 undergoes secondary transfer by a transfer roller 114 onto a sheet 110 conveyed from a storage tray 113.

The fixing processing mechanism of the present embodiment has a first fixer 150 and a second fixer 160 that apply heat and pressure to the toner image that has been transferred to the sheet 110, thereby causing it to be fixed to the sheet 110. The first fixer 150 includes a fixing roller 151 for applying heat to the sheet 110, a pressure belt 152 for causing the sheet 110 to press against the fixing roller 151, and a post-first-fixing sensor 153 that detects that the fixing is complete. The fixing roller 151 is a hollow roller that has a heater inside. Also, the rollers are driven by a motor (not shown), and thereby convey the sheet 110. The second fixer 160 is disposed further downstream in the conveyance direction of the sheet 110 than the first fixer 150. The second fixer 160 adds a gloss to the toner image on the sheet 110 that was fixed by the first fixer 150 and ensures fixedness. The second fixer 160 also has a fixing roller 161, a pressure roller 162, and a post-second-fixing sensor 163, similarly to the first fixer 150. Depending on the type of the sheet 110, it is not necessary to pass through the second fixer 160. In such a case, in order to reduce the amount of energy consumed, the sheet 110 passes through the conveyance path 130 without going through the second fixer 160. A conveyance path switching flapper 131 functions as a switching unit that switches between guiding the sheet 110 to the conveyance path 130 and guiding the sheet 110 to the second fixer 160.

A conveyance path switching flapper 132 is a guiding member that guides the sheet 110 to a discharging route 135 or to a discharging route 139 for discharge to the outside. A reversal sensor 137 is provided on a discharging route 135. The leading edge of the sheet 110 passes the reversal sensor 137 and is conveyed to a reversal unit 136. When the reversal sensor 137 detects the trailing edge of the sheet 110, the conveyance direction of the sheet 110 is switched. In other words, it switches from the conveyance direction indicated by arrow C to the conveyance direction indicated by arrow D. A conveyance path switching flapper 133 is a guiding member that guides the sheet 110 to a conveyance path 138 for double-sided image formation, or to the discharging route 135. A conveyance path switching flapper 134 is a guiding member that guides the sheet 110 to the discharging route 139 to the outside. Note that multiple conveyance rollers 140 are provided on the conveyance paths such as the discharging route 135 and the discharging route 139.

A color sensor 200 that detects the pattern image on the sheet 110 is disposed further downstream in the conveyance direction of the sheet 110 than the second fixer 160. The color sensor 200 functions as a color measuring unit that measures the color of an image fixed to a sheet further downstream in the conveyance direction of the sheet than the first fixer 150 and the second fixer 160. The color sensor 200 may be disposed on the discharging route 139, the conveyance path 138, or the conveyance path 130. When color measurement (color detection) is instructed by an instruction from the operation panel 180, the engine control unit 102 executes maximum density correction, tone correction, multicolor adjustment (ICC profile creation), and the like. Note that in maximum density correction and tone correction, the density of a monochrome measurement image is measured, and in multicolor adjustment, the color of a measurement image in which multiple colors are overlaid is measured.

In the present embodiment, the sheet on which the measurement image has been formed is conveyed from the conveyance path 130 to the discharging route 135 and pre-scanned by the color sensor 200. After pre-scanning is complete, the sheet is conveyed to the reversal unit 136. Here, the sheet feeding direction of the sheet is reversed. The sheet is conveyed in the opposite direction on the discharging route 135, is once again conveyed to the color sensor 200, and main scanning is executed. Note that after pre-scanning is complete, the sheet may be conveyed through another route and guided to the color sensor 200. For example, in order to form an image on both sides, namely a first side and a second side of a sheet, it is possible to use the conveyance path 138, which is a conveyance path for conveying a sheet on which an image has been formed on the first side. The conveyance sequence in this case is as follows: reversal unit 136=>conveyance route 138=>conveyance path 130=>discharging route 135=>reversal unit 136=>conveyance route 138=>conveyance route 130=>discharging route 135. In such a case, due to passing through the conveyance route 138 two times, the sheet passes the color sensor 200 a total of three times. This is because when it passes the color sensor 200 the first time, the first side on which the test pattern has been formed faces the color sensor 200, and when it passes the color sensor 200 the second time, the second side faces the color sensor 200. Thus, when the sheet passes the color sensor 200 the third time, main scanning is executed since the first side once again faces the color sensor 200. Note that it is important that the sheet on which the measurement image has been formed passes the color sensor 200 two times or more, and thereby pre-scanning is executed in the first passing time, and main scanning is executed in the second passing time. Because of this, the sheet may be conveyed on any type of conveyance route as long as the sheet passes the color sensor 200 two times or more.

In this way, the conveyance roller 140 functions as a conveyance unit that conveys a sheet (test chart) on which multiple measurement images (test patterns) have been formed. The color sensor 200 functions as a measuring unit that subjects multiple test patterns from a sheet being conveyed by the conveyance rollers 140 to pre-scanning and main scanning.

Color Sensor

The structure of a color separation type of color sensor 200 and a color measurement operation will be described next with reference to FIG. 2. Note that the color sensor is not limited to the description here, as long as it is capable of changing the accumulation time, which is a feature of the present embodiment. The accumulation time is an amount of time for which the color sensor 200 accumulates reflected light from the test pattern in a light receiving element.

Figure 2:
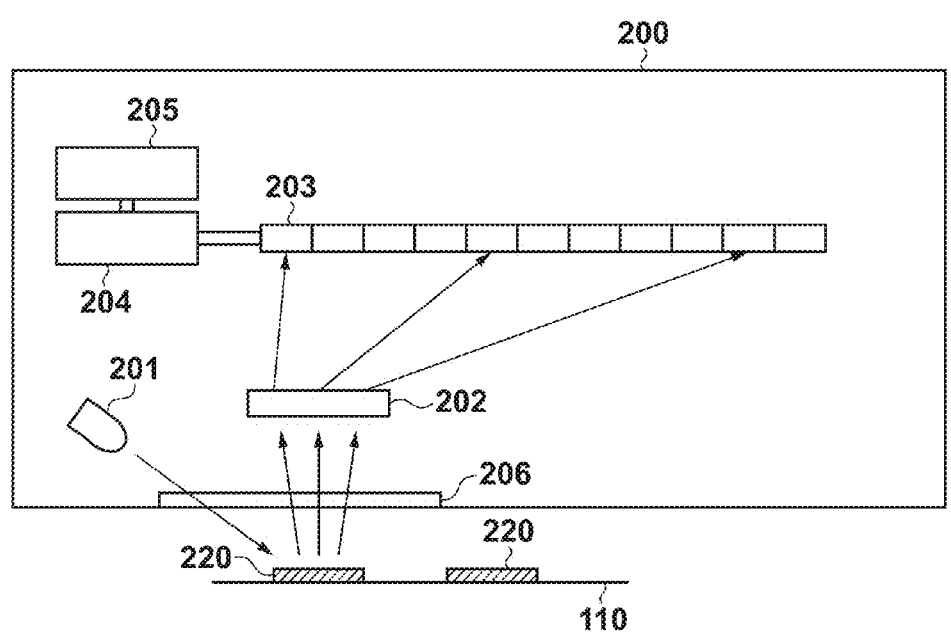
FIG. 2 is a schematic configuration diagram of a color sensor.

FIG. 2 is a diagram showing the structure of the color sensor 200. A white light LED 201 is a light emitting element that irradiates the test pattern 220 on the sheet 110 with light. A diffraction grating 202 is a color separation component that separates light that is reflected from the test pattern 220 and passes through a window 206 according to wavelength. A line sensor 203 is a light detecting element including n light receiving elements that detect light decomposed by the diffraction grating 202 for each wavelength. A calculation unit 204 performs various types of calculations based on light intensity values of pixels detected by the line sensor 203. A memory 205 stores various types of data that are to be used by the calculation unit 204. The calculation unit 204 has a color separation calculation unit that performs a color separation calculation based on the light intensity values, a Lab calculation unit that calculates Lab values, and the like. It is also possible to furthermore provide a lens that gathers light emitted from the white light LED 201 in the test pattern 220 on the sheet 110 and gathers light reflected from the test pattern 220 on the diffraction grating 202. The color sensor 200 measures the color of the test pattern 220 that is conveyed by a conveyance unit (conveyance rollers 140) that conveys a sheet. Note that if multiple color sensors 200 are installed as color measurers, a configuration is possible in which only one calculation unit 204 and memory 205 are provided for the multiple color sensors 200. This is because according to this, processes relating to color measurement values from the multiple color sensors 200 can be executed in an integrated manner and the load on the printer controller 103 can be reduced. Also, since the number of components can be reduced, it is possible to obtain an effect of reducing manufacturing cost.

Description of Various Operations

The image forming apparatus 100 has at least a normal image forming mode and a calibration mode. The normal image forming mode is a mode in which an image is formed according to a print job input from a host computer, and an image of an original that was scanned by an image scanner is formed. The calibration mode is a mode in which color reproduction and tone attributes of the image forming apparatus 100 are maintained in a desired state. Maximum density correction, tone correction, color matching profile creation, and the like are executed in the calibration mode.

Color Conversion Processing

Figure 3:
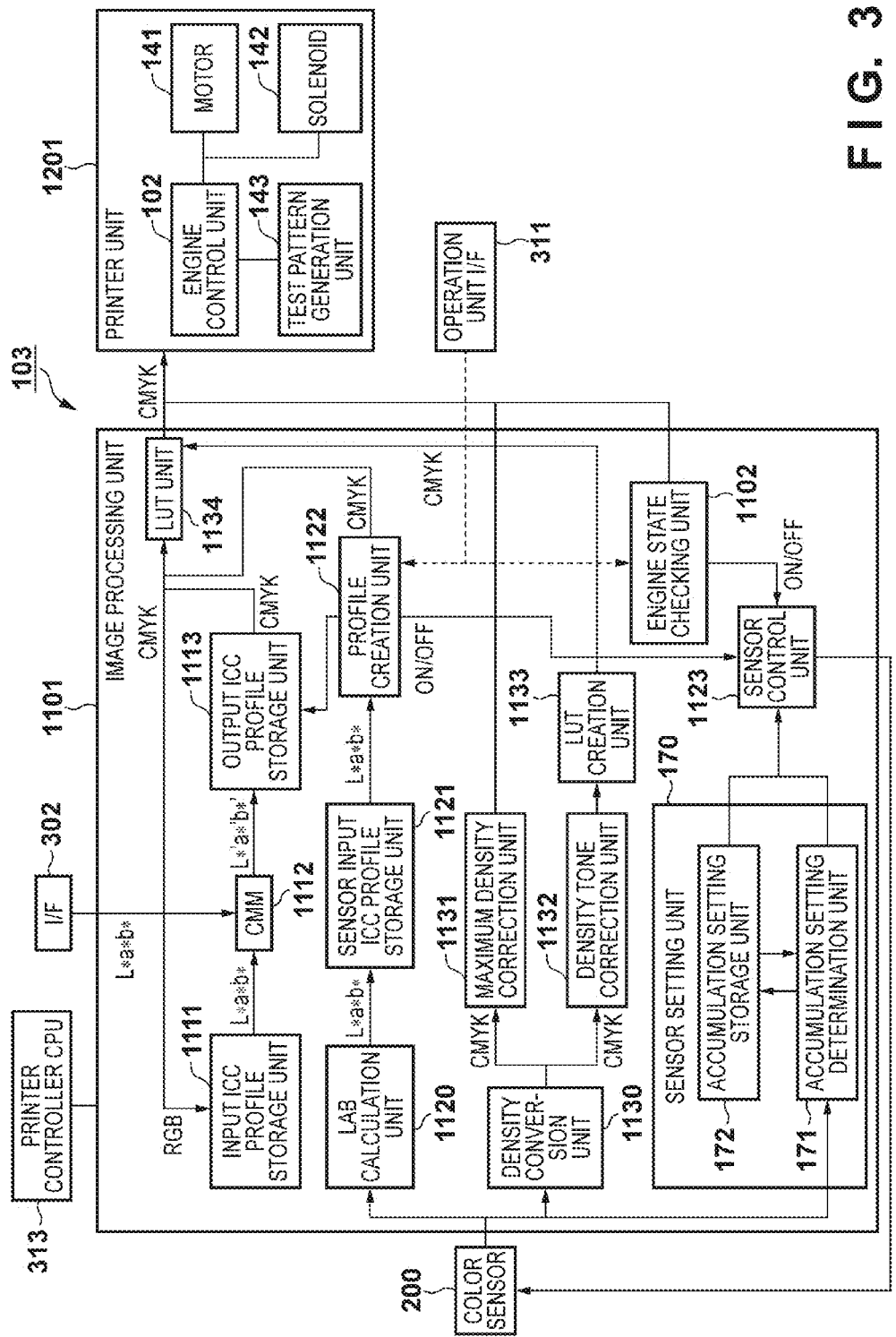
FIG. 3 is a schematic configuration diagram of a control unit.

Color conversion processing will be described below with reference to FIG. 3. When a color image is to be formed, an I/F 302 receives input of RGB image signal values from a host computer, the operation panel 180, an external memory, or the like. Note that an image signal envisioning a standard printing CMYK image signal such as Japan Color may be input. An input ICC profile storage unit 1111 for external input executes RGB→L*a*b* conversion or CMYK→L*a*b* conversion with respect to image signals input through the I/F 302. The input ICC profile storage unit 1111 executes color conversion using an input ICC profile. The input ICC profile is a one-dimensional LUT (Look-Up Table) that controls the gamma of input image signals, a multicolor LUT that is referred to as "direct mapping", a one-dimensional LUT that controls the gamma of generated conversion data, and the like. According to these tables, the input image signal is converted from a device-dependent color space into device-independent color value data (L*a*b* data). The image signal that was converted in the L*a*b* table color system is input into a CMM (color management module) 1112. The CMM 1112 executes GAMUT conversion, light source type mismatch (also known as color temperature setting mismatch) color conversion, and the like with respect to the input image signal. In GAMUT conversion, mismatches between the scanning color space of an external I/F functioning as an input device, and the output color reproduction range of the image forming apparatus 100 functioning as an output device are mapped. Light source type mismatch color conversion is color conversion for adjusting a mismatch between the light source type at the time of input and the light source type at the time of observing the output material. According to this, L*a*b* data is converted into L*'a*'b*' data. The L*'a*'b*' data is input into an output ICC output profile storage unit 1113 and is subjected to color conversion according to an output ICC profile stored therein. Accordingly, it is converted into an output device-dependent CMYK (Cyan Magenta Yellow Black) signal and is output to an LUT unit 1134. The LUT unit 1134 corrects the tone of the CMYK signal values using the LUT created by an LUT creation unit 1133 and outputs the resulting signal to the printer unit 1201. The engine control unit 102 of the printer unit 1201 controls the exposure units (lasers 108) of the four stations 120, 121, 122, and 123, and causes a latent image to be formed on the photosensitive drum 105. The engine control unit 102 forms a toner image on a sheet and causes it to be discharged to the exterior while controlling a motor 141 that causes the conveyance rollers 140 to rotate, and controlling a solenoid 142 in order to switch conveyance paths.

Calibration Mode

A calibration execution instruction from the operation panel 180 is input to an engine state checking unit 1102 through an operation unit I/F 311. Note that the input data from the operation panel 180 may first be input to a printer controller CPU 313. Functions of the engine state checking unit 1102 may be realized by the printer controller CPU 313. When a transition to the calibration mode is instructed by the printer controller CPU 313, the engine state checking unit 1102 instructs the printer unit 1201 to output the test chart and instructs a sensor control unit 1123 to perform color measurement. The test chart is the sheet on which test patterns have been formed. The engine control unit 102 causes test pattern image data to be output to a test pattern generation unit 143 in accordance with the calibration instruction. The test pattern generation unit 143 may be installed in the image processing unit 1101.

In the calibration mode, the color sensor 200 executes pre-scanning and main scanning. Pre-scanning is processing for scanning test patterns in order to adjust the accumulation times (also referred to as the scanning times, exposure times, or measurement times) for the respective test patterns (respective colors) in the color sensor 200. Main scanning is processing for scanning test patterns using the accumulation times determined through the pre-scanning, for maximum density correction, tone correction, or profile creation. In pre-scanning, an accumulation setting determination unit 171 in the sensor setting unit 170 determines the accumulation time for each test pattern based on the test pattern scanning results (spectral reflectance and amount of reflected light) obtained by the color sensor 200. The accumulation setting storage unit 172 stores the accumulation times that were determined for the test patterns. The sensor control unit 1123 reads out the accumulation times corresponding to the test patterns when main scanning is to be executed and controls the accumulation times of the color sensor 200. The accumulation time may be a numeric value, or it may be a symbol such as accumulation setting 1, 2, or 3. Image processing conditions and image forming conditions are adjusted based on the scanning result (spectral reflectance) of the color sensor 200 acquired by the main scanning.

In this way, in the calibration mode, test patterns are formed on a sheet based on an image signal generated by the test pattern generation unit 143, the test patterns are scanned by the color sensor 200, and the image processing conditions and image forming conditions are adjusted. A maximum density correction unit 1131 corrects the maximum density based on CMYK signal values (density values) obtained by a density conversion unit 1130 furthermore converting the scanning result (spectral reflectance) of the color sensor 200. A charging potential, a developing potential, an exposure amount, and the like are examples of parameters for correcting the maximum density. A density/tone correction unit 1132 calculates a correction amount for exposure settings according to which a desired tonality is obtained, based on the CMYK signal values (density values) of the test patterns. The LUT creation unit 1133 creates an LUT in accordance with the correction amount of the exposure setting. Also, the scanning result (spectral reflectance) of the color sensor 200 is converted into Lab values by the Lab calculation unit 1120, converted using the profile stored in an input ICC profile storage unit 1121 for the color sensor, and input to a profile creation unit 1122. The profile creation unit 1122 performs characterization (multicolor CAL) for creating a profile, which is a multicolor LUT for suppressing multicolor variation. It is envisioned that an ICC (International Color Consortium) profile that has been accepted in the marketplace in recent years is used here as the profile for realizing superior color reproduction. The present invention can be applied to a color matching profile other than an ICC profile as well. Examples of this include a CRD (Color Rendering Dictionary) employed from PostScript Level 2 or a color separation table in Photoshop (registered trademark) provided by Adobe, Inc., or a CMYK simulation in ColorWise by EFI, Inc. that preserves blackboard information. The profile creation unit 1122 may create the profile in accordance with the method disclosed in Japanese Patent Laid-Open No. 2009-004865, for example. Maximum density correction, tone correction, and profile creation will not be explained in detail here since it is possible to use a technique that is already publicly known.

Example of Test Pattern

FIG. 4 is a diagram showing an example of YMCK signals for generating test patterns included in a test chart. YMCK signals for 81 types of test patterns are shown in FIG. 4, but the number of test patterns may be changed according to the application of the test chart. For example, there are 928 test patterns in an ISO 12642 test form (test chart).

Pre-Scanning Sequence

In order to describe pre-scanning, pre-scanning that is executed in a multicolor CAL will be described here. However, pre-scanning and main scanning in the present invention can be applied as pre-scanning and main scanning in maximum density correction and tone correction. This is because pre-scanning is for setting the accumulation time of the color sensor 200 for each test pattern, and is not dependent on how the scanning result of the color sensor 200 is to be used. The color measurement speed, test pattern size, and sensor settings that will be described below are merely examples for facilitating understanding of the description.

Necessity of Pre-Scanning

Pre-scanning is a task of determining a color measurement condition of the color sensor 200 in a color measurement step for performing multicolor CAL. The color measurement condition mentioned here is the accumulation setting (accumulation time) of the color sensor 200. The color measurement condition is a condition needed for accurately measuring the color of a test pattern. In summary, the accumulation time t is a measurement time for which the amount of reflected light incident on the color sensor 200 from the test patterns is appropriate.

In the present embodiment, there are three accumulation setting levels for the sake of simplifying the description. The amount of time for measuring a test pattern one time in the respective accumulation settings are, for example, as follows.

Accumulation setting 1: 3 ms
Accumulation setting 2: 6 ms
Accumulation setting 3: 12 ms A method for determining the accumulation setting for the test patterns will be described here. Test patterns having a high density (dark portions) and test patterns having a low density (light portions) in FIG. 4 will be compared below.

Figure 5A:
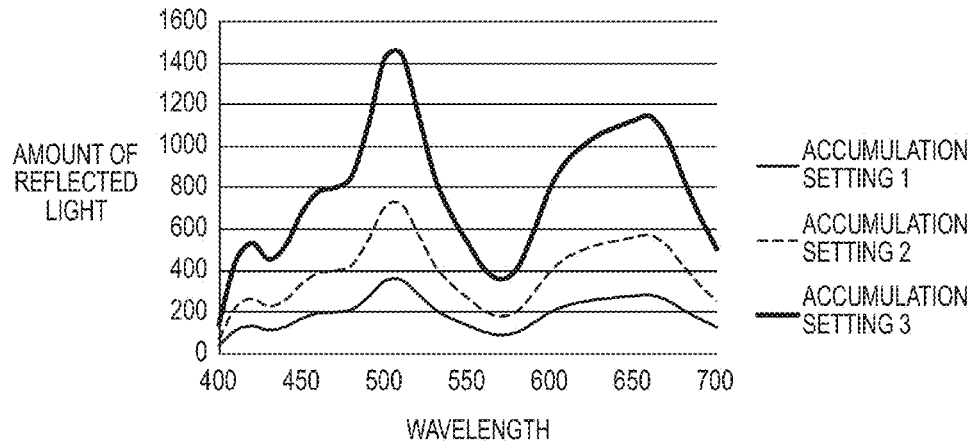
FIGS. 5A and 5B are diagrams showing an amount of reflected light with respect to wavelength and accumulation time.
Figure 5B:
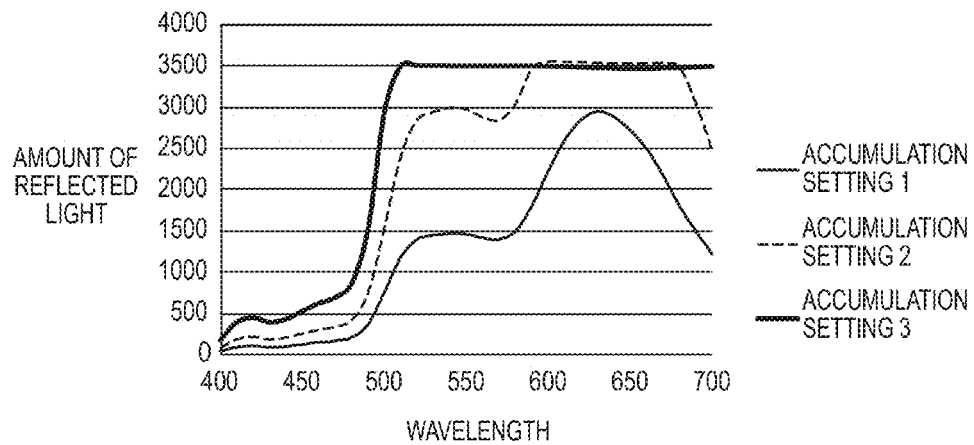

FIGS. 5A and 5B are diagrams showing the relationship between accumulation time differences and the amount of reflected light. The horizontal axis indicates the wavelength and the vertical axis indicates the amount of reflected light. In particular, FIG. 5A shows the relationship between the accumulation time and the amount of reflected light with respect to a test pattern whose pattern number is number 81, which is a representative example of a dark portion test pattern. FIG. 5B shows the relationship between the accumulation time and the amount of reflected light with respect to a test pattern whose pattern number is number 13, which is a representative example of a light portion test pattern. Note that FIGS. 5A and 5B show the amount of reflected light with respect to the three accumulation settings.

The amount of reflected light here is obtained by subtracting a dark output value from the amount of light that is reflected from the test pattern and is incident on the color sensor 200. The dark output value refers to an output value from the color sensor 200 obtained when the light source of the color sensor 200 does not emit light.

As shown in FIG. 5A, it is clear that the amount of reflected light increases as the exposure time increases for the dark portion test pattern number 81. Also, it can be determined that accumulation setting 3 is appropriate for the dark portion test pattern number 81. In general, if there is a small amount of reflected light, the percentage of the noise component with respect to the electrical signal is large. Accordingly, it can be said that accumulation setting 3 by which the widest dynamic range possible can be obtained is appropriate.

On the other hand, it can be determined that the accumulation setting 1 is appropriate for the light portion test pattern number 13. It should be noted that if the wavelength is 600 nm or above in the accumulation setting 2, the amount of reflected light will be saturated. If the wavelength reaches 500 nm or above in the accumulation setting 3, the reflected light is saturated. This is caused by the amount of reflected light plateauing at around 3500 due to the fact that the signal value indicating the amount of reflected light is limited to 4096, and the fact that the dark output value is 596. Thus, there is an appropriate accumulation time for each of the 81 test patterns that are to be used for multicolor correction.

Although only test patterns having high and low densities have been described here as an example, appropriate settings for accumulation times are needed for other test patterns as well. This is because if the state of the image forming apparatus 100 changes, the colors of the test patterns change successively as well. Accordingly, pre-scanning is executed before color measurement in order to determine the appropriate accumulation times, and thus color measurement can be performed accurately. Also, it is possible to maintain color reproduction at a high degree of accuracy by using the color sensor 200 in which the appropriate accumulation time has been set. Note that pre-scanning is a step of determining an accumulation setting before a pattern is actually measured, and when color measurement is to actually be performed, color is measured multiple times using the determined accumulation settings in order to average out microscopic irregularities in the pattern surface and raise the accuracy of color measurement. In the present embodiment, after pre-scanning has ended for all test patterns, main scanning is executed using the accumulation settings determined through the pre-scanning.

Pre-Scanning Timing and Accumulation Setting Determination Flow

Figure 6:
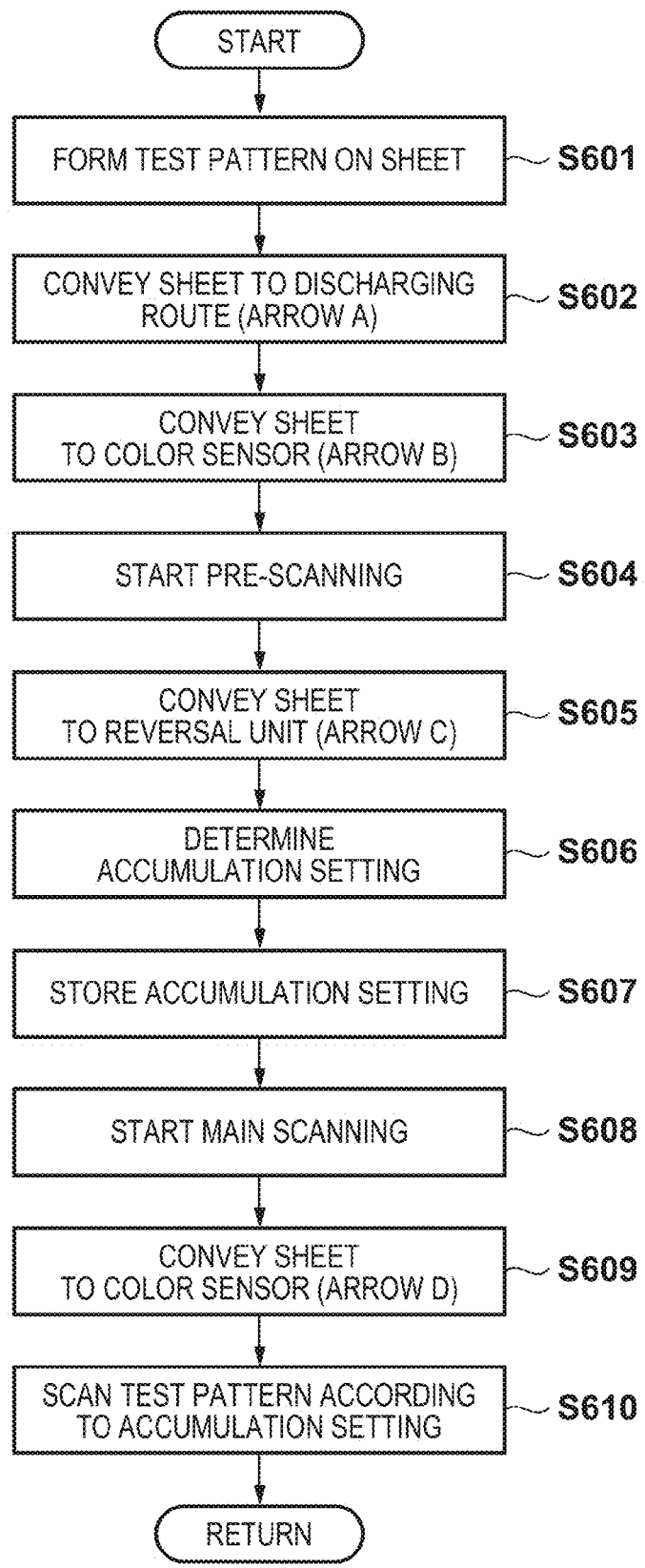
FIG. 6 is a flowchart showing steps for pre-scanning and main scanning.

The timing at which to perform pre-scanning and a flow for determining the accumulation settings will be described with reference to FIGS. 1, 3, and 6. Here, the execution of the multicolor CAL is instructed from the operation panel 180. Also, as a general rule, the printer controller CPU 313 is what mainly performs processing.

In step S601, test patterns for multicolor CAL are formed on a sheet, and thereby a test chart is formed. For example, the printer controller CPU 313 instructs the engine control unit 102 to generate test patterns. In response to the instruction, the engine control unit 102 causes the test pattern generation unit 143 to generate test pattern image signals. The engine control unit 102 performs control of the stations 120 to 123 according to the image signals in order to form electrostatic latent images, develop the electrostatic latent images into toner images, and transfer the toner images onto a sheet. The engine control unit 102 furthermore performs control of the first fixer 150 in order to fix the toner image on the sheet. Accordingly, the test chart, which is a sheet on which multiple test patterns have been formed, is complete.

In step S602, after being output from the first fixer 150, the test chart is conveyed in the direction indicated by arrow A shown in FIG. 1. For example, the printer controller CPU 313 instructs the engine control unit 102 to convey the test chart to the conveyance route 130. The engine control unit 102 uses a motor 141 to drive the conveyance roller 140 while driving the solenoid 142 to perform control of the flapper 131. Accordingly, the test chart is conveyed in the direction indicated by the arrow A shown in FIG. 1, and the test chart is guided to the conveyance route 130.

In step S603, the test chart is conveyed in the direction indicated by arrow B shown in FIG. 1. For example, the printer controller CPU 313 instructs the engine control unit 102 to convey the test chart to the discharging route 135. The engine control unit 102 uses the motor 141 to drive the conveyance roller 140 while driving the solenoid 142 to perform control of the flapper 132. Accordingly, the test chart is conveyed in the direction indicated by the arrow B shown in FIG. 1, and the test chart is guided from the conveyance route 130 to the discharging route 135.

In step S604, the color sensor 200 starts pre-scanning. For example, the printer controller CPU 313 instructs the sensor control unit 1123 via the engine state checking unit 1102 to perform pre-scanning. The sensor control unit 1123 sets the pre-scanning accumulation times that were determined in advance at the time of factory shipping in the color sensor 200. For example, the sensor control unit 1123 switches between the three accumulation settings 1, 2, and 3 in that order for each test pattern. Accordingly, it is possible to obtain measurement results for the three accumulation settings 1, 2, and 3 for each test pattern. Note that the color sensor 200 measures color (spectral reflectance and amount of reflected light) based on the test patterns on the test chart that is conveyed at a predetermined conveyance speed by the conveyance rollers 140.

In step S605, the test chart is conveyed in the direction indicated by arrow C shown in FIG. 1. For example, the printer controller CPU 313 instructs the engine control unit 102 to convey the test chart to the reversal unit 136. The engine control unit 102 uses the motor 141 to drive the conveyance roller 140 while driving the solenoid 142 to perform control of the flapper 133. Accordingly, the test chart is conveyed in the direction indicated by the arrow C shown in FIG. 1, and the test chart is guided from the discharging route 135 to the reversal unit 136. When the reversal sensor 137 detects the trailing edge of the test chart, the engine control unit 102 stops the motor 141. Also, the sensor control unit 1123 ends pre-scanning.

In step S606, the accumulation setting determination unit 171 determines the accumulation setting for each test pattern based on the pre-scanning result. For example, upon receiving an instruction to determine the accumulation settings from the printer controller CPU 313, the accumulation setting determination unit 171 compares the three pre-scanning results obtained for each test pattern with a predetermined threshold value (saturation determination). Accordingly, the accumulation setting determination unit 171 identifies the largest pre-scanning result that does not exceed the threshold value among the three pre-scanning results corresponding to the accumulation settings 1, 2, and 3 and determines the accumulation setting (accumulation time) according to the identified pre-scanning result. Accordingly, the dynamic range of the color sensor 200 can be widened for each test pattern. In step S607, the accumulation setting determination unit 171 stores the accumulation settings for the respective test patterns in the accumulation setting storage unit 172 in accordance with an instruction from the printer controller CPU 313.

In step S608, the printer controller 103 instructs the sensor control unit 1123 via the engine state checking unit 1102 to start main scanning. The sensor control unit 1123 sets the accumulation setting for each test pattern that is stored in the accumulation setting storage unit 172 in the color sensor 200. The color sensor 200 executes main scanning while changing the accumulation setting according to the test pattern that is the scanning target.

In step S609, the test chart is conveyed in the direction indicated by arrow D shown in FIG. 1. For example, the printer controller CPU 313 instructs the engine control unit 102 to convey the test chart to the discharging route 135. The engine control unit 102 uses the motor 141 to drive the conveyance roller 140 while driving the solenoid 142 to perform control the flapper 133. Accordingly, the test chart is conveyed in the direction indicated by the arrow D shown in FIG. 1, and the test chart is guided from the reversal unit 136 to the discharging route 135. Accordingly, the test chart is conveyed in the opposite direction on the discharging route 135 and is conveyed toward the color sensor 200.

In step S610, the color sensor 200 references the accumulation settings for the respective test patterns and executes main scanning. Data regarding the amount of reflected light obtained by main scanning is sent to the Lab calculation unit 1120. Subsequently, the profile creation unit 1122 creates a profile based on the main scanning results. Thereafter, the test chart is discharged to the outside via the discharging route 139. Note that the colors of the test patterns are measured in opposite orders in pre-scanning and main scanning. Accordingly, the color measurement conditions (accumulation times) set in the color sensor 200 are in opposite orders as well. For example, it is presumed that scanning starts from test pattern number 1 and test pattern number 81 is scanned last in pre-scanning. In this case, scanning will start from test pattern number 81 and test pattern number 1 will be scanned last in main scanning.

Averaging Process Execution Count in Main Scanning

It is desirable to use the lowest number of sheets possible to form the test chart. This is because as the number of sheets forming the test chart that is the target of color measurement is increased, it is more time-consuming to output the test chart and user downtime will increase. Needless to say, the number of sheets needed will increase as well. Downtime is time (waiting time) during which the user cannot form an image using the image forming apparatus 100.

In view of this, the present embodiment describes a method for enabling color measurement values to be calculated accurately while reducing the number of test chart sheets. Note that the color measurement speed, pattern size, and sensor settings that will be described below are examples, and it is not the case that the present invention is limited to these alone.

First, pattern size is calculated according to an equation such as the following:

$$S = PS \times t \times N \qquad \text{Equation 1}$$

Here, PS is the conveyance speed (mm/s) of the sheet on which the test pattern has been formed. t is the accumulation time (s) that is needed to obtain an appropriate amount of reflected light from the test pattern that is incident on the color sensor 200 in the test patterns. N is the number of times color measurement needs to be performed in order to average out the irregularities of microscopic regions in the test patterns. In the present embodiment, PS is presumed to be 250 mm/s for the sake of convenience in the description. The accumulation time t and the averaging process execution count N are different for each test pattern. There are three setting (accumulation setting) levels for the accumulation time t, and appropriate values are set for the respective test patterns.

The averaging process execution count N is the number of times that color measurement needs to be performed (number of times sampling is performed) in order to average out irregularities in microscopic regions in the test patterns. By setting an appropriate averaging process execution count N, color measurement accuracy is improved. In the present embodiment, there are three levels of settings for the averaging process execution count N (e.g., 4 times, 8 times, 16 times), and the appropriate value is selected for each test pattern. The averaging process execution count N that is appropriate for each test pattern is determined in advance at the time of factory shipping and stored in the memory 205.

Figure 7:
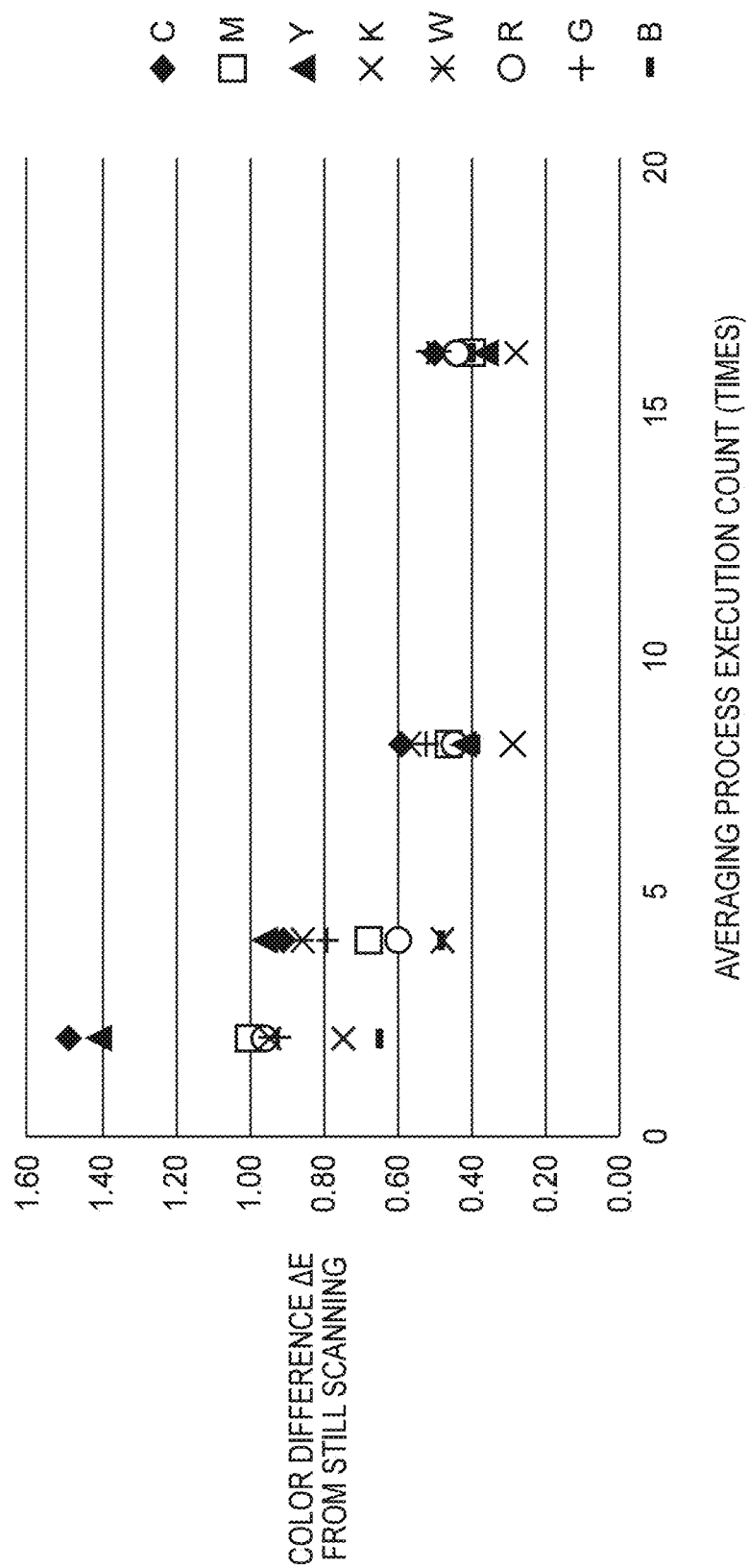
FIG. 7 is a diagram showing color difference with respect to averaging process execution count.

FIG. 7 shows the relationship between the averaging process execution count N and a color difference ΔE for CMYKWRGB test patterns. CMYKWRGB indicates cyan, magenta, yellow, black, white, red, green, and blue. The vertical axis indicates the color difference ΔE between a value obtained by measuring a CMYKWRGB test pattern in a resting state and a value obtained by measuring the color of the test pattern while the test chart on which the test pattern has been recorded is conveyed. The horizontal axis indicates the averaging process execution count N. This is the number of measured values (can also be referred to as the number of times measurement is performed and the number of times sampling is performed) that are obtained by measuring the color of a test pattern while the test chart is conveyed and are used when the average value of test pattern measurement values is to be calculated. Note that color difference data in the case where the averaging process execution count is 2 is shown in FIG. 7 for comparison.

It is clear from looking at FIG. 7 that as the averaging process execution count N is increased, the color difference ΔE with respect to still scanning decreases. In other words, it is clear that as the averaging process execution count N is increased, the accuracy of color measurement increases.

It is clear that test patterns with low luminosity, such as black (K) and blue (B), have a smaller amount of change in the color difference ΔE compared to other test patterns with higher luminosity. It can be said that this is most prominent when the averaging process execution counts are 8 and 16. Since the accumulation times for test patterns with low luminosity are longer, the region that is measured is larger to begin with than the measurement regions of other test patterns. Accordingly, even in the case where the averaging process execution count is low, it is easy to accurately detect test patterns with low luminosity.

Upon performing a test such as that described above for multiple patterns that include the 81 test patterns shown in FIG. 4, the appropriate averaging process execution count for each accumulation setting was as follows.

Accumulation setting 1: 16 times
Accumulation setting 2: 16 times
Accumulation setting 3: 8 times Test Pattern Layout A method for obtaining the test pattern size for each accumulation setting will be described using the above-described Equation 1. First, the sum of the measurement times needed for the respective accumulation settings is obtained using the averaging process execution count.

Accumulation setting 1: 3 ms*16=48 ms
Accumulation setting 2: 6 ms*16=96 ms
Accumulation setting 3: 12 ms*8=96 ms From these results, it is clear that the longest accumulation time is 96 ms. In other words, the size (length in the conveyance direction) of each test patterns need only be 250*0.096=24 mm or more. In the present embodiment, consideration is given to ±2 mm for example as a margin with respect to an image instability region in a test pattern. Accordingly, the size of each test pattern is 28 mm (40 mm in main scanning direction). Note that in pre-scanning, the test patterns are scanned once with each of the accumulation settings 1, 2, and 3, in that order. The lengths in the conveyance direction of the respective multiple measurement images are determined based on a length that is obtained by multiplying the sheet conveyance speed, the number of samples per measurement image, and the sum of the different accumulation times together. If the above-mentioned numerical values are substituted into the equation, the sum is 21 ms (using 1 as the number of samples). Accordingly, the length in the conveyance direction is a value (7.25 mm) obtained by adding a margin to 5.25 mm. In this example, the length in the conveyance direction required for pre-scanning is shorter than the length in the conveyance direction required for main scanning, and therefore the size of each test pattern is determined according to the latter.

Figure 8:
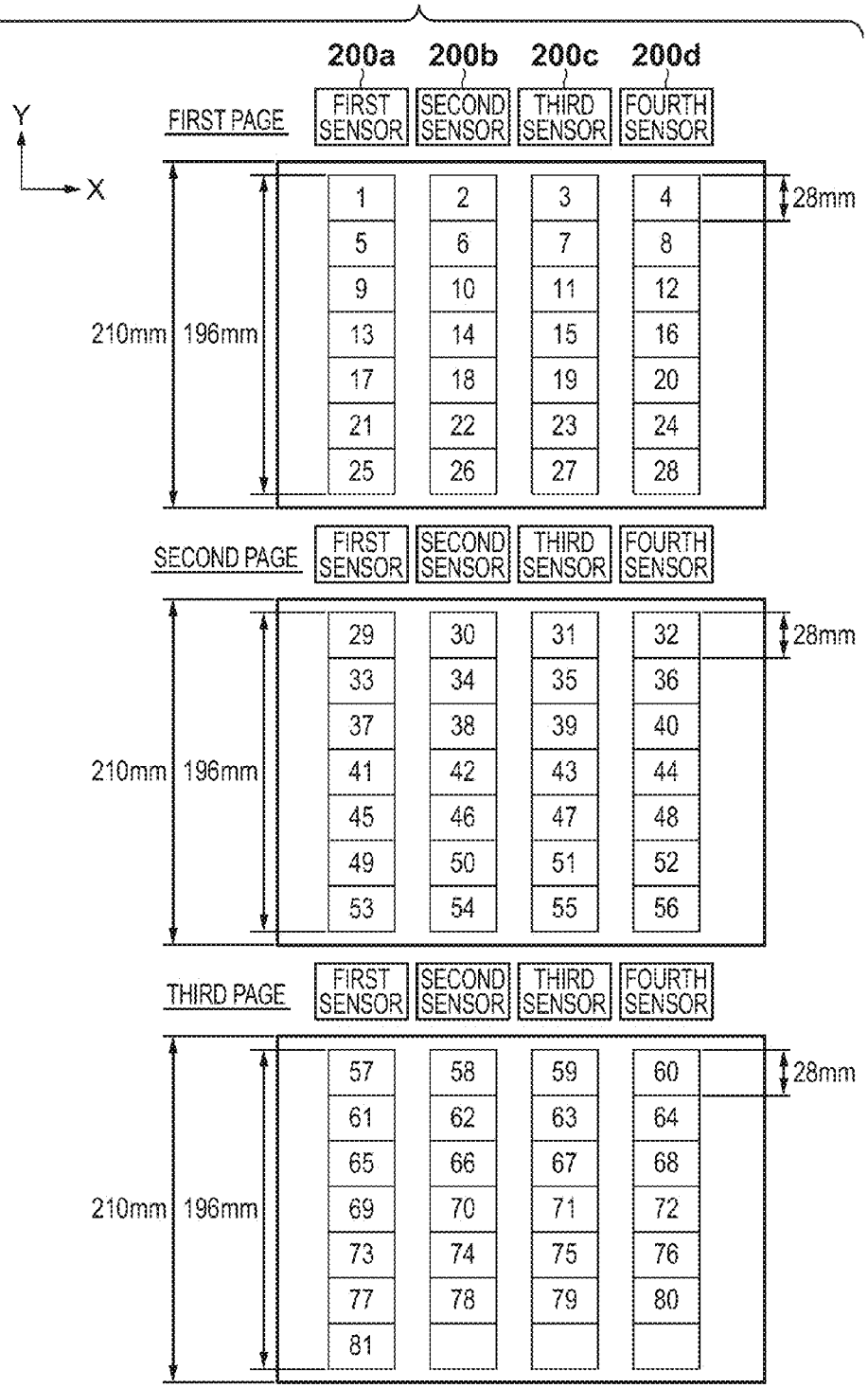
FIG. 8 is a diagram showing an example of a test chart according to an embodiment.

FIG. 8 shows an example of a test pattern layout in the case where four color sensors 200 according to the present embodiment are aligned in the conveyance direction. The four color sensors 200 will be referred to here as a first sensor 200a, a second sensor 200b, a third sensor 200c, and a fourth sensor 200d. Also, the Y direction shown in FIG. 8 is the sheet conveyance direction and the X direction is the direction that is orthogonal to the conveyance direction. Also, the three sheets are all A4 sheets.

Figure 9:
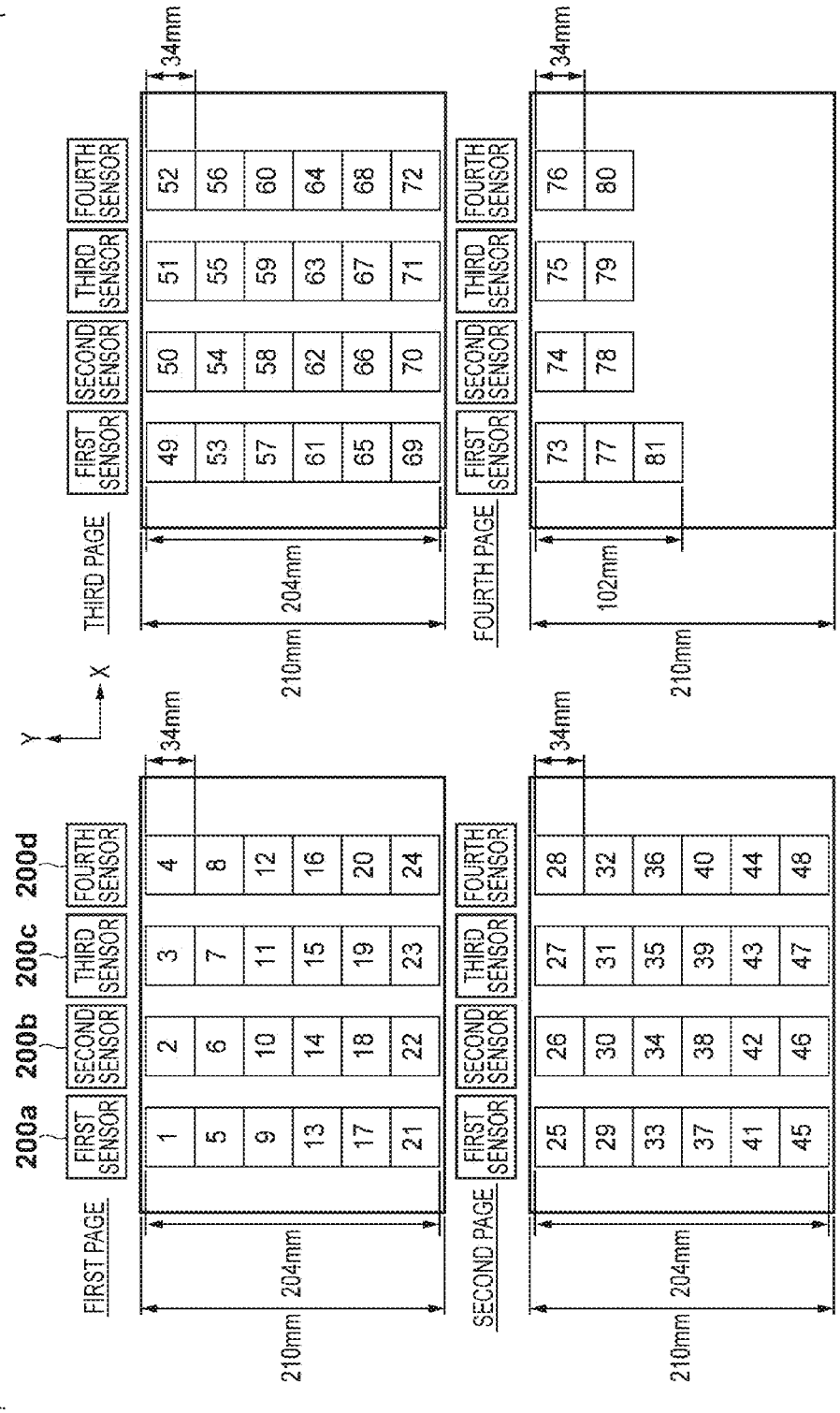
FIG. 9 is a diagram showing an example of a test chart according to a comparative example.

FIG. 9 shows an example of a test pattern layout according to a comparative example. In the comparative example, pre-scanning and main scanning are executed when the test pattern is conveyed in the direction of the arrow B shown in FIG. 1. Because of this, the color measurement time for pre-scanning is added to the color measurement time for main scanning, and as a result, the size per test pattern increases. As described above, the accumulation time is changed to each level from level 1 to level 3 in pre-scanning. The color measurement time for pre-scanning needs to be 3+6+12=21 ms. Accordingly, the longest color measurement time per test pattern is 96+21=117 ms. Also, the pattern size needs to be 250*0.117=29.25 mm or more. Furthermore, with consideration given to the margin, the ultimate size (length in the conveyance direction) of each test pattern is around 34 mm. Accordingly, as shown in FIG. 8, four A4 sheets in total are needed in the comparative example. In other words, in the present embodiment, the number of sheets can be reduced in comparison to the comparative example.

Thus, in the present embodiment, after pre-scanning for all measurement images is complete, the sheet is conveyed once again toward the color sensor 200 and main scanning is executed. In other words, by conveying the sheet on which the measurement images have been recorded to the color sensor 200 two times or more, it is possible to establish a color measuring technique that can reduce the number of sheets, as well as suppress an increase in the size of the measurement images. Also, since the number of test patterns is not reduced, the accuracy of the color measurement can be maintained at a high degree.

There are several methods for conveying the sheet to the color sensor 200 two times or more. For example, after the sheet passes the color sensor 200 for pre-scanning, the engine control unit 102 controls the motor 141 such that the sheet conveyance direction is reversed, and thereby the sheet is conveyed to the color sensor 200 for main scanning. The conveyance routes used in this case include a route that directly leads from the reversal unit 136 to the discharging route 135, a route that guides the sheet from the reversal unit 136 to the conveyance route 138 using the flapper 133, passes through the conveyance route 130 once again, and leads to the discharging route 135, or the like. In the case of the latter route, the engine control unit 102 guides the sheet to the conveyance route 138 by driving the solenoid 142 to switch the flapper 133.

The color sensor 200 was described as being arranged on the discharging route 135 for conveying the sheet with an image formed on the first side has been formed in order to form an image on both sides, namely the first side and the second side, of the sheet. However, the color sensor 200 may be arranged on any of the discharging route 139, the conveyance route 130, the reversal unit 136, and the conveyance route 138. In short, the color sensor 200 can be installed on any conveyance route that is downstream of the first fixer 150.

The accumulation setting determination unit 171 functions as a determination unit according to which the accumulation time that is the longest among different accumulation times in a range in which saturation does not occur in the pre-scanning results is determined as the accumulation time for main scanning. The dynamic range can be widened due to the accumulation time that is the longest in a range in which saturation does not occur in the pre-scanning results being determined as the accumulation time for main scanning. In other words, the accuracy of color measurement can be maintained at a high degree.

The test pattern may be any of a measurement image for creating an ICC profile, a measurement image for correcting the maximum density of an image to be formed by the image forming apparatus, or a measurement image for correcting tone attributes of an image formed by the image forming apparatus. Needless to say, the present invention can be applied to any test pattern for adjusting a parameter related to image formation.

In Embodiment 1, one test pattern underwent pre-scanning using multiple accumulation times. On the other hand, in Embodiment 2, one test pattern undergoes pre-scanning using one out of multiple accumulation times and the measurement results corresponding to the remaining multiple accumulation times are estimated. Accordingly, it is possible to furthermore shorten the lengths in the conveyance direction of the test patterns and to increase the number of times sampling is performed. Note that the description of portions that are the same as Embodiment 1 will not be repeated.

Pre-Scanning Using Shortest Accumulation Time

Figure 10:
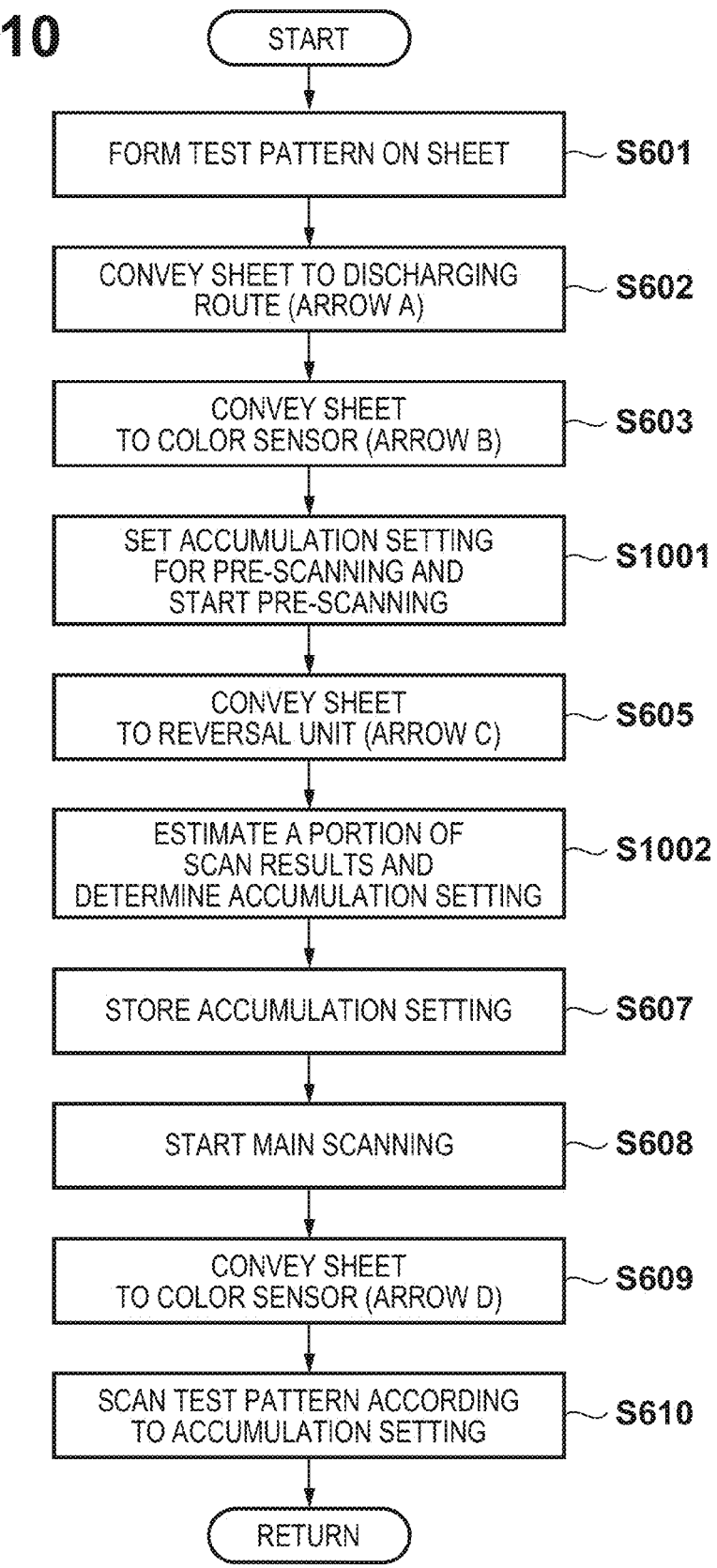
FIG. 10 is a flowchart showing steps for pre-scanning and main scanning.

FIG. 10 is a flowchart showing pre-scanning and main scanning for Embodiment 2. Note that steps that have already been described are denoted by the same reference numerals. After executing steps S601 to S603, the procedure moves to step S1001.

In step S1001, the color sensor 200 starts pre-scanning. For example, the printer controller CPU 313 instructs the sensor control unit 1123 via the engine state checking unit 1102 to perform pre-scanning. The sensor control unit 1123 sets the pre-scanning accumulation time that was determined in advance at the time of factory shipping in the color sensor 200. For example, the sensor control unit 1123 sets a pre-set accumulation setting (e.g., accumulation setting 1) among the three accumulation settings 1, 2, and 3 in the color sensor 200. The color sensor 200 outputs a measurement result for one accumulation time for each test pattern. Here, three accumulation setting levels are provided for main scanning, and accumulation setting 1, which is the lowest of the three accumulation setting levels is used in pre-scanning. The accumulation times for accumulation settings 1, 2, and 3 are the same as those described above. Thereafter, step S605 is executed, and the procedure moves to step S1002.

In step S1002, the accumulation setting determination unit 171 estimates the pre-scanning results for accumulation settings 2 and 3 based on the pre-scanning result for accumulation setting 1 and determines the accumulation settings of the respective test patterns based on the pre-scanning results for accumulation settings 1, 2, and 3. In Embodiment 1, by changing the accumulation setting to each level from level 1 (3 ms) to level 3 (12 ms) in order and determining whether or not saturation (plateauing) occurs in the detected values (reflected light amounts) of the color sensor 200, the accumulation setting determination unit 171 determines the appropriate optimal accumulation setting. The detected value of the color sensor 200 configured by a CMOS sensor or the like changes linearly in proportion to the accumulation time. For example, if the exposure time doubles, the detected value also substantially doubles, and if the exposure time is halved, the detected value is also substantially halved. Note that in actuality, a noise component is also included in the detected value of the color sensor 200. Because of this, the degree of accuracy in the detection of the color sensor 200 is raised by adjusting the exposure time so that the widest dynamic range possible can be obtained. Thereafter, steps S607 to S610 are executed.

In the present embodiment, a pre-scanning result is obtained for the lowest accumulation setting, and the pre-scanning results for the other accumulation settings are estimated using the linear relationship between the exposure time and the detected value. For example, the pre-scanning results of the accumulation settings 2 and 3 can be calculated using the following equations.

Pre-scanning result for accumulation setting 2=pre-scanning result for accumulation setting 1×(accumulation time for accumulation setting 2/accumulation time for accumulation setting 1)

Pre-scanning result for accumulation setting 3=pre-scanning result for accumulation setting 1×(accumulation time for accumulation setting 3/accumulation time for accumulation setting 1)

Accordingly, in Embodiment 2 as well, results that are similar to those in Embodiment 1 can be obtained. Furthermore, Embodiment 2 is superior to Embodiment 1 in the following regard. In Embodiment 1, pre-scanning was executed once per test pattern for each accumulation setting. On the other hand, in the present embodiment, pre-scanning may be performed multiple times (e.g., three times) per test pattern, and the median value may be used. Note that if the sizes of the test patterns are the same as those in Embodiment 1 and Embodiment 2, pre-scanning can be performed up to 7 times at most ((3 ms+6 ms+12 ms)/3 ms=7). In Embodiment 1, irregularities in microscopic regions tend to accumulate in the test patterns since pre-scanning is performed only once. In the present embodiment, the influence of irregularities can be reduced since pre-scanning is performed multiple times. If the influence of irregularities can be reduced, the accuracy of pre-scanning increases, and as a result, the accuracy of main scanning also increases. Ultimately, it is possible to increase the accuracy of the LUT and ICC profile for maximum density and tone correction determined using the result of scanning the test patterns. Note that the pre-scanning execution count can be set appropriately with consideration given to the conveyance speed, test pattern size, and scan time per execution. Also, although a description was given in which the median value of multiple measured values were used, the pre-scanning result may be an average value, and it is possible to use a lowest or highest value.

In this way, according to Embodiment 2, the color sensor 200 executes pre-scanning using the accumulation time that is the shortest among multiple different accumulation times that are provided in advance. The longest accumulation time among the multiple different accumulation times in a range in which saturation does not occur in the result of the pre-scanning performed by the color sensor 200 is determined by the accumulation time determination unit 171 based on the pre-scanning result obtained using the minimum accumulation time. For example, among the multiple different accumulation times, the pre-scanning results for the remaining accumulation times other than the shortest accumulation time are estimated based on a linearity relation between the accumulation time and the pre-scanning results of the color sensor 200, the shortest accumulation time, and the pre-scanning results thereof. In other words, the accumulation time and the pre-scanning result can be expressed as a linear function. The slope of the linear function can be obtained based on the shortest accumulation time and the corresponding pre-scanning result. The values of intercepts are determined at the time of factory shipping. Accordingly, if the remaining accumulation times other than the shortest accumulation time are substituted into the linear function, the corresponding pre-scanning result can be calculated (estimated). By applying the saturation determination to the pre-scanning results for the multiple accumulation times obtained in this way, the longest accumulation time in a range in which saturation does not occur in the pre-scanning result can be determined. Although a description using the shortest accumulation time among the different accumulation times was given here, another accumulation time may be used.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-027143, filed Feb. 14, 2013 which is hereby incorporated by reference herein in its entirety.

What is claimed is:

1. An image forming apparatus comprising:
an image forming unit configured to form a measurement image on a sheet;
a conveyance unit configured to convey the sheet;
a measurement unit configured to measure the measurement image by accumulating reflected light from the measurement image on the sheet conveyed by the conveyance unit;
a control unit configured to control the image forming unit to form the measurement image on the sheet, control the conveyance unit to convey the sheet on which the measurement image is formed toward the measurement unit, control the measurement unit to execute a first scan during which the measurement unit measures the measurement image formed on the sheet, control the conveyance unit to convey the sheet on which the measurement image is formed toward the measurement unit again, and control the measurement unit to execute a second scan during which the measurement unit measures the measurement image formed on the sheet; and
a determination unit configured, based on a measurement result of the measurement unit in the first scan, to determine a reflected light accumulation time during which the measurement unit accumulates reflected light from the measurement image in the second scan,
wherein the control unit executes the first scan using one reflected light accumulation time among a plurality of different reflected light accumulation times provided in advance, and
the determination unit estimates another measurement result corresponding to another reflected light accumulation time based on a linearity relation between the reflected light accumulation time and the measurement result, the predetermined reflected light accumulation time, and the measurement result obtained using the predetermined reflected light accumulation time in the first scan, and identifies a highest measurement result in a range in which saturation does not occur from among the plurality of measurement results, and determine the reflected light accumulation time corresponding to the identified measurement result to be the reflected light accumulation time for the second scan,
wherein each of a plurality of measurement results corresponds to a different one of the reflected light accumulation time.

2. The image forming apparatus according to claim 1, wherein the control unit controls the conveyance unit such that after the sheet passes the measurement unit for the first scan, the conveyance direction of the sheet is reversed, so as to convey the sheet to the measurement unit for the second scan.

3. The image forming apparatus according to claim 1, wherein the measurement image is a measurement image for creating profile data, a measurement image for correcting the maximum density of an image to be formed by the image forming apparatus, or a measurement image for correcting a tone attribute of an image to be formed by the image forming apparatus.

4. The image forming apparatus according to claim 1, wherein the measurement unit measures an amount of light from the measurement image according to each wavelength region of reflected light.

5. The image forming apparatus according to claim 4, further comprising:
a calculation unit configured to calculate the spectral reflectance of the measurement image based on measurement results of the measurement image obtained by the measurement unit.

6. The image forming apparatus according to claim 1, wherein
the conveyance unit includes a reverse part, and
the conveyance unit reverses the conveyance direction of the sheet by switchbacking the sheet at the reverse part for the second scan.

7. The image forming apparatus according to claim 1, further comprising:
a converting unit configured convert an image signal based on a converting condition; and
an updating unit configured to update the converting condition based on the measurement result of the second scan,
wherein the image forming unit forms the image based on the image signal converted by the converting unit.

8. The image forming apparatus according to claim 1, wherein the measurement unit includes:
an irradiating unit configured to irradiate the measurement image with light;
a diffraction grating configured to disperse the light reflected by the measurement image; and
a line sensor configured to receive the light dispersed by the diffracting grating.

9. An image forming apparatus comprising:
an image forming unit configured to form a plurality of measurement images including a first measurement image and a second measurement image, on a sheet;
a conveyance unit configured to convey the sheet;
a measurement unit configured to measure the plurality of measurement images on the sheet based on a measurement condition;
a controller configured to control the image forming unit to form the plurality of measurement images on the sheet, control the conveyance unit to convey the sheet toward the measurement unit, control the measurement unit to execute a first scan during which the measurement unit measures each of the plurality of measurement images, control the conveyance unit to convey the sheet toward the measurement unit again, and control the measurement unit to execute a second scan during which the measurement unit measures the each of the plurality of measurement images; and
a determination unit configured to determine a first measurement condition for measuring the first measurement image in the second scan based on a measurement result of the first measurement image by the measurement unit in the first scan, and determine a second measurement condition for measuring the second measurement image in the second scan based on a measurement result of the second measurement image by the measurement unit in the first scan.

10. The image forming apparatus according to claim 9, wherein the measurement unit includes an optical-receiver configured to receive a reflected light from the measurement image,
the measurement unit is further configured to measures a light reception amount of the optical-receiver corresponding to the reflected light from the measurement image,
the measurement condition is a time period during which the optical-receiver receives the reflected light from the measurement image,
the light reception amount increases in a case where the time period increase, and
the light reception amount decreases in a case where the time period decrease.

11. The image forming apparatus according to claim 10, wherein the controller is further configured to execute the first scan using a first time period and a second time period longer than the first time period.

12. The image forming apparatus according to claim 9, wherein a length of the measurement image in a conveyance direction in which the conveyance unit conveys the sheet is determined based on a conveyance speed of the sheet, the number of sampling, and the time period.

13. The image forming apparatus according to claim 9, wherein the measurement unit includes a light irradiating unit configured to irradiate the plurality of measurement images with light, and an optical-receiver configured to receive a reflected light from the measurement image,
the measurement unit is further configured to measures a light reception amount of the optical-receiver corresponding to the reflected light from the measurement image,
the measurement condition is a time period during which the light irradiating unit irradiates the measurement image with the light,
the light reception amount increases in a case where the time period increase, and
the light reception amount decreases in a case where the time period decrease.

14. The image forming apparatus according to claim 9, wherein the controller uses a plurality of measurement conditions to execute the first scan.

15. The image forming apparatus according to claim 9, wherein the conveyance unit includes a reverse part, and
the conveyance unit is further configured to reverse the conveyance direction of the sheet by switchbacking the sheet at the reverse part, after the sheet passes the measurement unit in the first scan.

16. The image forming apparatus according to claim 9, wherein the measurement result of the first measurement image by the measurement unit includes an amount of reflected light from the first measurement image corresponding to a first wavelength region and an amount of reflected light from the first measurement image corresponding to a second wavelength region different from the first wavelength region, and
the measurement result of the second measurement image by the measurement unit includes an amount of reflected light from the second measurement image corresponding to the first wavelength region and an amount of reflected light from the second measurement image corresponding to the second wavelength region.

17. The image forming apparatus according to claim 9,
wherein the measurement unit is further configured to measure a spectral reflectance of the first measurement image in the second scan and measure a spectral reflectance of the second measurement image in the second scan.

18. The image forming apparatus according to claim 9, further comprising:
a converting unit configured to convert an image signal based on a converting condition, and
an updating unit configured to update the converting condition based on the measurement results in the second scan,
wherein the image forming unit is further configured to form an image based on the image signal converted by the converting unit.

19. The image forming apparatus according to claim 9,
wherein the measurement unit includes:
an irradiating unit configured to irradiate the measurement image with light;
a diffraction grating configured to disperse the light reflected by the measurement images; and
a line sensor configured to receive the light dispersed by the diffracting grating.

* * * * *